(12) United States Patent
Tibbe et al.

(10) Patent No.: US 7,828,968 B2
(45) Date of Patent: *Nov. 9, 2010

(54) METHOD AND APPARATUS FOR IMAGING TARGET COMPONENTS IN A BIOLOGICAL SAMPLE USING PERMANENT MAGNETS

(75) Inventors: Arjan G. J. Tibbe, Deventer (NL); Leon W. M. M. Terstappen, Huntingdon Valley, PA (US)

(73) Assignee: Veridex, LLC, Raritan, NJ (US)

( * ) Notice: Subject to any disclaimer, the term of this patent is extended or adjusted under 35 U.S.C. 154(b) by 155 days.

This patent is subject to a terminal disclaimer.

(21) Appl. No.: 12/031,807

(22) Filed: Feb. 15, 2008

(65) Prior Publication Data

US 2009/0061477 A1 Mar. 5, 2009

Related U.S. Application Data (63) Continuation-in-part of application No. 11/897,471, filed on Aug. 30, 2007.

(51) Int. Cl.
*B03C 1/02* (2006.01)
*B03C 1/30* (2006.01)
(52) U.S. Cl. .......................... 210/222; 209/39; 436/63
(58) Field of Classification Search .................. None
See application file for complete search history.

(56) References Cited

U.S. PATENT DOCUMENTS

| | | | |
|---|---|---|---|
| 4,465,377 A | 8/1984 | DeBruyne | |
| 5,374,531 A * | 12/1994 | Jensen | 435/7.24 |
| 6,409,925 B1 * | 6/2002 | Gombinsky et al. | 210/695 |
| 6,500,549 B1 * | 12/2002 | Deppisch et al. | 428/425.5 |
| 6,620,627 B1 | 9/2003 | Liberti et al. | |
| 6,623,982 B1 | 9/2003 | Liberti et al. | |
| 6,645,731 B2 | 11/2003 | Terstappen et al. | |
| 6,861,259 B2 | 3/2005 | Columbus | |
| 7,011,794 B2 | 3/2006 | Kagan et al. | |

FOREIGN PATENT DOCUMENTS

| | | |
|---|---|---|
| WO | WO02077604 | 10/2002 |
| WO | WO03018757 | 3/2003 |
| WO | WO03019141 | 3/2003 |
| WO | WO03065042 | 8/2003 |
| WO | WO03069421 | 8/2003 |
| WO | WO2006102233 | 9/2006 |

* cited by examiner

*Primary Examiner*—Rebecca E. Prouty
*Assistant Examiner*—Paul C. Martin (57) ABSTRACT

A system for enumeration of cells in fluids by image cytometry is described for assessment of target populations such as leukocyte subsets in different bodily fluids or bacterial contamination in environmental samples, food products and bodily fluids. Briefly, fluorescently labeled target cells are linked to magnetic particles or beads. In one embodiment, a small, permanent magnet is inserted directly into the chamber containing the labeled cells. The magnets are coated with PDMS silicone rubber to provide a smooth and even surface which allows imaging on a single focal plane. The magnet is removed from the sample and illuminated with fluorescent light emitted by the target cells captured by a CCD camera. In another embodiment, a floater having a permanent magnet allows the target cells to line up along a single imaging plane within the sample solution. Image analysis can be performed with a novel algorithm to provide a count of the cells on the surface, reflecting the target cell concentration of the original sample.

5 Claims, 10 Drawing Sheets

Magnetic fluorescent beads

Figure 5

Labeled CD14-FF and Labeled CD45-APC

A

B    Floater    Tube    Cap

CTC's

METHOD AND APPARATUS FOR IMAGING TARGET COMPONENTS IN A BIOLOGICAL SAMPLE USING PERMANENT MAGNETS

CROSS REFERENCE TO RELATED APPLICATIONS

This application is a non-provisional application, which is incorporated by reference herein and claims priority, of U.S. Ser. No. 11/897,471, filed Aug. 30, 2007 from which this application is a continuation-in-part.

FIELD OF THE INVENTION

The invention relates generally to imaging target components in a fluidic (biological) sample. More specifically, methods and apparatus are described that provide for the positive selection of target cells in a blood sample. Small permanent magnets are added directly to a blood sample containing CD4 immunomagnetic labeled fluorescently stained Acridine Orange (AO) whole blood.

BACKGROUND ART

The use of immunomagnetic separation technology provides greater sensitivity and specificity in the detection of target entities in blood for example, but not limited to, intact circulating cancer cells and endothelial cells. This simple and sensitive diagnostic tool, as described (U.S. Pat. No. 6,365,362; U.S. Pat. No. 6,551,843; U.S. Pat. No. 6,623,982; U.S. Pat. No. 6,620,627; U.S. Pat. No. 6,645,731; WO 02/077604; WO03/065042; and WO 03/019141) can be used in the present invention to correlate the statistical survivability of an individual patient based on a threshold level.

A prior diagnostic tool incorporates a blood sample from a cancer patient (WO 03/018757) incubated with magnetic beads, coated with antibodies directed against an epithelial cell surface antigen as for example EpCAM. After labeling with anti-EpCAM-coated magnetic nanoparticles, the magnetically labeled cells are then isolated using a magnetic separator. The immunomagnetically enriched fraction is further processed for downstream immunocytochemical analysis or image cytometry, for example, in the CELLSPOTTER™ or CELLTRACKS® System, both fluorescent cell imaging systems (Immunicon Corp., USA). The magnetic fraction can also be used for downstream immunocytochemical analysis, RT-PCR, PCR, FISH, flowcytometry, or other types of image cytometry.

The CELLSPOTTER™ or CELLTRACKS® fluorescent imaging systems utilizes immunomagnetic selection and separation to highly enrich and concentrate any epithelial cells present in whole blood samples. The captured cells are detectably labeled with a leukocyte specific marker and with one or more tumor cell specific fluorescent monoclonal antibodies to allow identification and enumeration of the captured CTC's as well as instrumental or visual differentiation from contaminating non-target cells. At an sensitivity of 1 or 2 epithelial cells per 7.5 ml of blood, this assay allows tumor cell detection even in the early stages of low tumor mass.

EASYCOUNT® system (PCT/US03/04468) is a fluorescent imaging system, designed to make a distinction between lymphocytes, granulocytes and monocytes. The system includes a compact electronic optical instruments, analytical methods, image acquisition, and data reduction algorithms for the detection and enumeration of magnetically labeled target cells or particles. Using whole blood as an example, blood cells are fluorescently labeled using one or more target specific fluorescent dyes, such as a DNA staining dye. The cells of interest or target cells in the blood sample are labeled by incubation with monoclonal antibodies conjugated to ferromagnetic particles. The sample is then placed into an appropriate optical detection chamber or covet, which in turn is placed into a magnetic field gradient that selectively causes the magnetically labeled cells to move towards the planar viewing surface of the chamber. The target cells are collected and immobilized substantially uniformly on the optically transparent surface of the chamber. A segment of this surface and the labeled target cells thereon are illuminated by means of one or more LED (light emitting diodes). Subsequently, the light emitted by individual target cells is captured by a CCD (charge coupled device). Image acquisition methods, processing methods, and algorithms, disclosed herein, are used to count the number of captured light-emitting cells and to relate the data output to the target cells per microliter of the analysis sample in the chamber and ultimately to the original specimen.

Currently available methods do not provide a rapid, low cost and consistently reliable means for assessing a target population of cells by flow or image cytometry. Thus, there is a clear need for quick and accurate detection of target components in blood such as cancer or endothelial cells.

SUMMARY OF THE INVENTION

The present invention is a method and means for positive selecting and imaging target entities. This includes a coated permanent magnetic device for magnetic manipulation in the system of the present invention. The system immunomagnetically concentrates the target entity, fluorescently labels, identifies and quantifies target cells by positive enumeration. Subsequent statistical analysis enables the clinician to obtain potential diagnostic information.

More specifically, the present invention provides the apparatus, methods, and kits for diagnosing disease disorders after immunomagnetic imaging. After obtaining a whole blood sample from a patient, a small permanent magnet is added to the whole blood sample. Unlike previously described magnetic presentation device CELLSPOTTER MAGNEST™ configuration, a small NdFeB magnet is directly added to a sample container, for example the cartridge in the CELLTRACKS® imaging device U.S. Pat. No. 6,861,259 and U.S. Pat. No. 7,011,794 with 100 ul of CD4 immunomagnetically labeled and fluorescently stained AO whole blood. After 10 minutes the small permanent magnet is pulled out of the sample using an iron rod or another magnet. The magnet is positioned within the container to allow for image analysis.

A further embodiment of the present invention has the magnet fixed to a floatation device (floater) within the reaction chamber. After addition of the reagents, blood and floater, the immunomagnetically labeled target cells are positioned along a single imaging plane for analysis, all within the reaction chamber.

DETAILED DESCRIPTION OF THE INVENTION

Immunomagnetic isolation, enrichment, and analysis in blood combines immunomagnetic enrichment technology and immunofluorescent labeling technology with an appropriate analytical platform after initial blood draw. The associated test has the sensitivity and specificity to detect rare cells in a sample of whole blood with the utility to investigate their role in the clinical course of the disease such as malignant tumors of epithelial origin.

With this type of technology, circulating tumor cells (CTC) have been shown to exist in the blood in detectable amounts Image cytometric analysis such that the immunomagnetically enriched sample is analyzed by the CELLSPOTTER™ or CELLTRACKS® fluorescent imaging systems utilizes a fluorescence-based microscope image analysis system, which in contrast with flowcytometric analysis permits the visualization of events and the assessment of morphologic features to further identify objects (U.S. Pat. No. 6,365,362).

The CELLSPOTTER™ and CELLTRACKS® System refers to an automated fluorescence microscopic system for automated enumeration of isolated cells from blood. The system contains an integrated computer controlled fluorescence microscope and automated stage with a magnetic yoke assembly that will hold a disposable sample cartridge. The magnetic yoke is designed to enable ferrofluid-labeled candidate tumor cells within the sample chamber to be magnetically localized to the upper viewing surface of the sample cartridge for microscopic viewing. Software presents target cells, labeled with antibodies to cytokeratin and having epithelial origin, to the operator for final selection.

Isolation of target cells can be accomplished by any means known in the art. After magnetic separation, the cells bound to the immunomagnetic-linked antibodies are magnetically held at the wall of the tube. Unbound sample is then aspirated and an isotonic solution is added to resuspend the sample. A nucleic acid dye, monoclonal antibodies to cytokeratin (a marker of epithelial cells) and CD 45 (a broad-spectrum leukocyte marker) are incubated with the sample. After magnetic separation, the unbound fraction is again aspirated and the bound and labeled cells are resuspended in 0.2 ml of an isotonic solution. The sample is suspended in a cell presentation chamber and placed in a magnetic device whose field orients the magnetically labeled cells for fluorescence microscopic examination. Cells are identified automatically and candidate target entities presented to the operator for checklist enumeration. An enumeration checklist consists of predetermined morphologic criteria constituting a complete cell.

Figure 1:
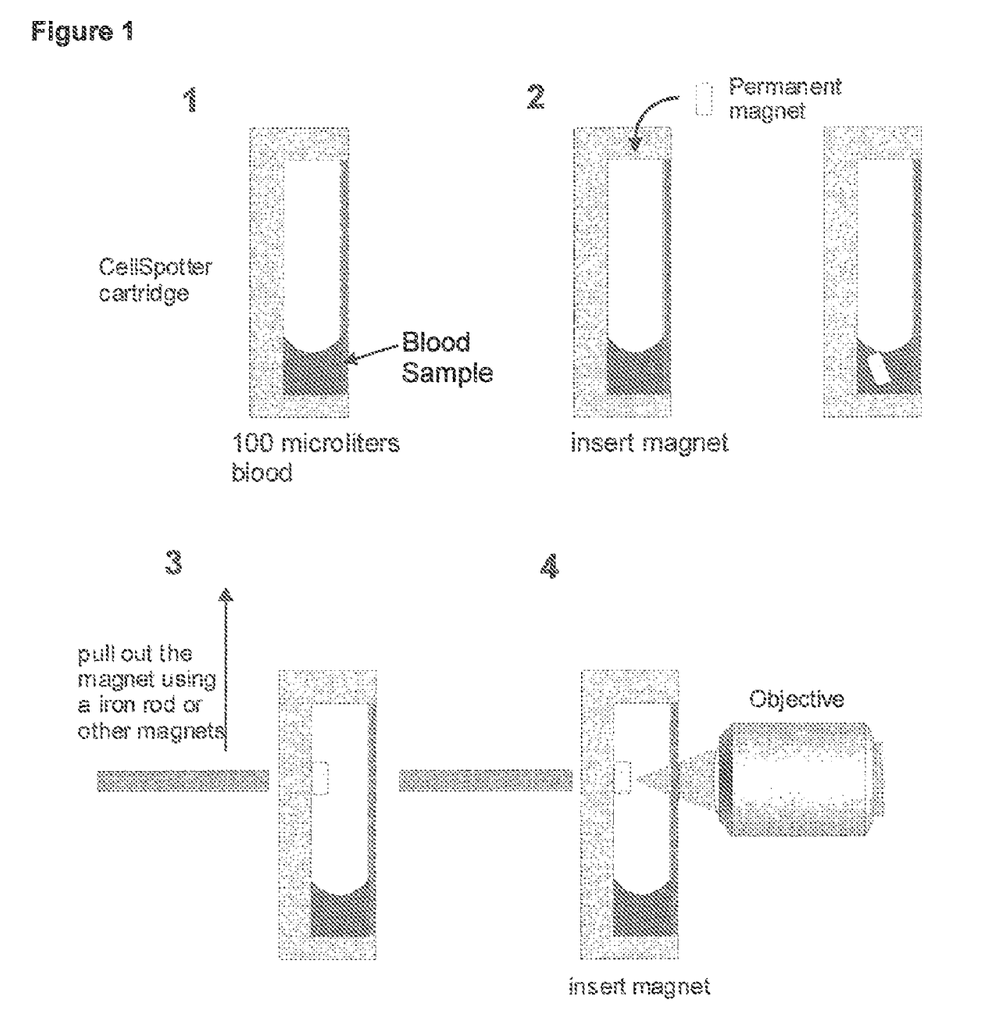
FIG. 1: Steps in the immunomagnetic imaging of target cells using the CELLSPOTTER™ cartridge as the imaging container.

The present invention utilizes a small magnet added directly to the immunomagnetically labeled target entity in a blood sample. The target is further labeled with imaging nucleic acid dyes, cell membrane, and/or cytoskeletal immunofluorescent labels. For example, FIG. 1 depicts a method for imaging CD4 expressing target cells in a whole blood sample. A small neodymium (NdFeB) permanent magnet is added to a whole blood sample after immunomagnetically labeled and fluorescently labeled for CD4. After 10 minutes, the small permanent magnet is separated from the fluid sample and within the sample container to be viewed through a viewing surface.

Figure 2:
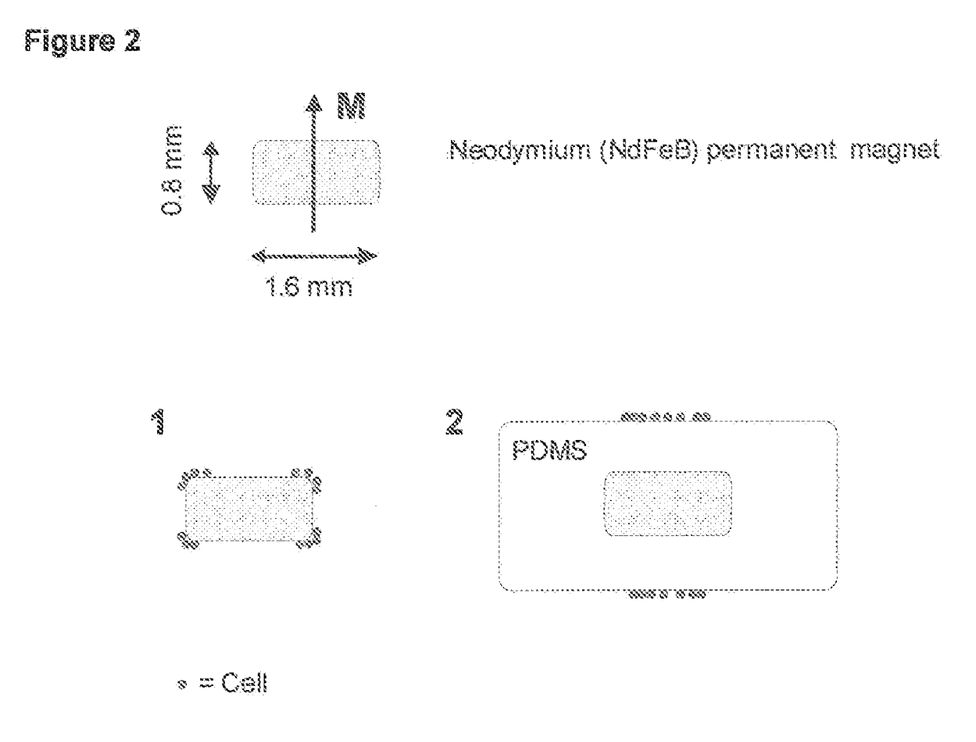
FIG. 2: Schematic representation of one embodiment of the small magnet where M represents the direction of the magnetic field. Panel 1 shows the target entity (cells). Panel 2 shows the target entity oriented on the PDMS silicone rubber coated magnet.

In one embodiment, the magnet is a disc with a diameter of 1.6 mm and a height of 0.8 mm (see FIG. 2). The smaller magnets are more preferred for this invention. Using this magnet, the target entity (cells) attach to only the magnets. The cells are not in a single focal plane and quality images are difficult to obtain. The same method is accomplished using encapsulated magnets with PDMS silicone rubber. The cells attach along a single focal plane. The layer of PDMS on the top of the magnet is approximately 1 mm. The width of the PDMS is approximately 3 mm.

There is a further need to design a method for moving the magnet in and out of the cell suspension as the chance of losing the magnets while moving in and out the suspension is large. The magnet must be small enough to reduce the force needed to pull it out of the cell suspension. The friction force between the wall of the chamber and the magnet may be too large to pull the magnet out of the cell suspension as the direction of movement is perpendicular to the magnetic force. Even with the size of the enclosure for the magnet enlarged, cells may move to the pole of the magnet and impede detection.

Figure 3:
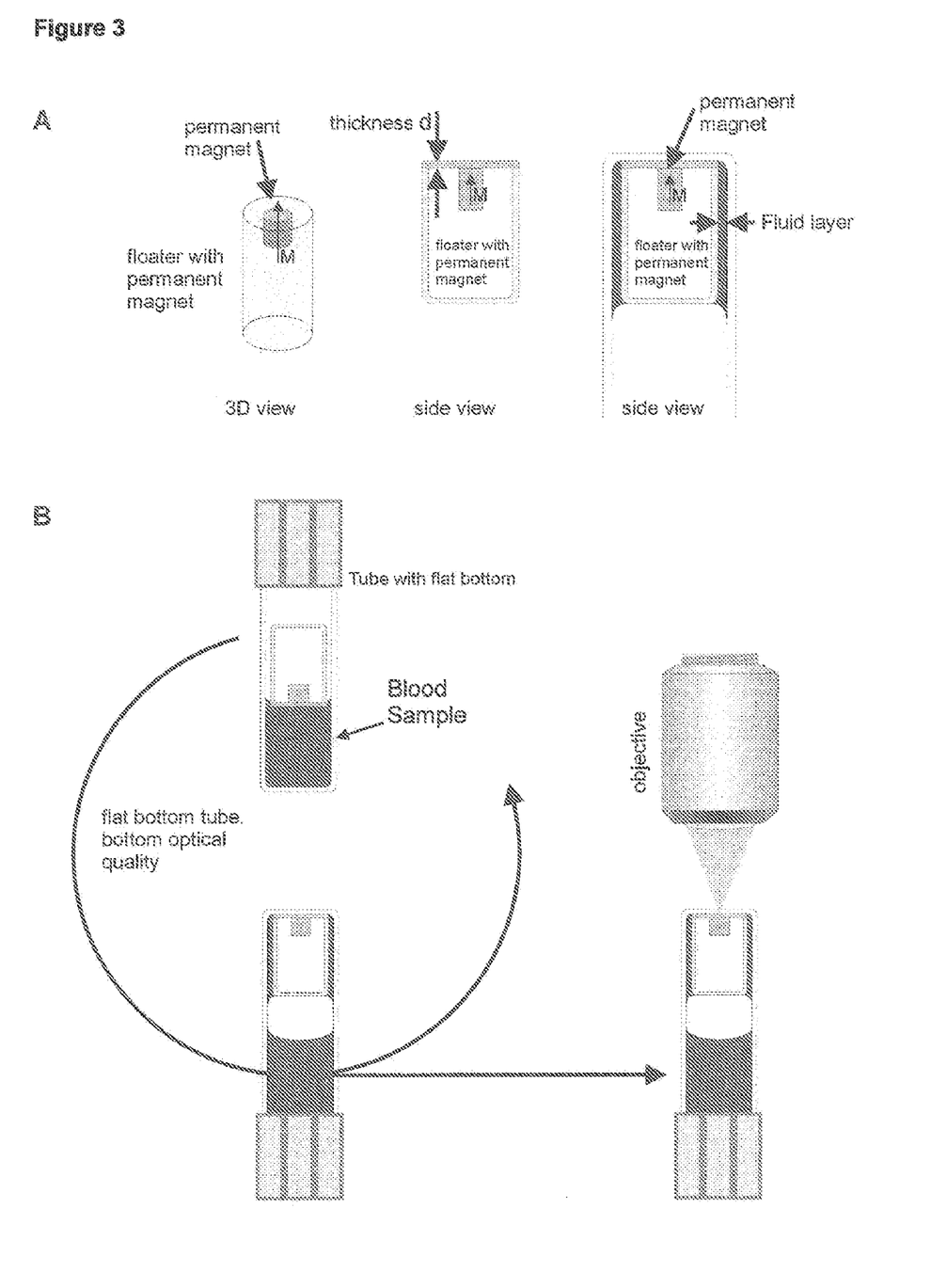
FIG. 3: (A) shows the design of the floater with the permanent magnet affixed to one face where M represents the direction of the magnetic field. (B) shows the floater inside a tube chamber having a flat optically transparent window for imaging.

These problems are considered with a further embodiment described in the present invention. FIG. 3 shows the basic steps of the present method. A permanent magnet is mounted on the inside of one face of a hollow tube, closed on all sides as shown in FIG. 3A. The face, having the magnet mounted, has a defined thickness (d). The surface can be flat or contain structures that facilitate capture and visibility of the objects of interest and limit the influence of interfering components in the fluid, i.e. free unbound magnetic particles.

The thickness of the face determines the spread of the cells on the outside. The height/diameter ratio of the floater determines the magnetic field's effect on the outside area of the floater. Consequently, the ratio should limit the influence of the magnetic field to approximately the face of the outside of the floater where the magnet is mounted.

A cell suspension is injected into a tube with a flat surface, having an optically transparent window. Immunomagnetic particles are added together with fluorescence labels. After incubation the floater containing the permanent magnet is inserted in the tube with the magnet facing the bottom of the tube and the tube is closed.

Alternatively, the floater can be inserted at the same time as the other reagents. By putting the test tube upside down the floater rises to the outside the fluid. A small layer of fluid is left in between the test tube and the floater which is neglect able to the total volume. Suspension is incubated with the reagents without interference of the floater or interferences of the magnetic field.

After incubation the tube is placed on a test tube rotator or similar device to cause the floater to move up and down through the cell suspension as illustrated in FIG. 3B. After enough time to allow complete capture of the magnetically labeled objects (cells), the tube is taken off the rotator and placed up-side down to force the floater to rise to toward the optical window on the flat surface of the tube. Using a standard fluorescence microscope, the cells, presented on the face of the floater are imaged through the bottom of the tube.

Figure 4:
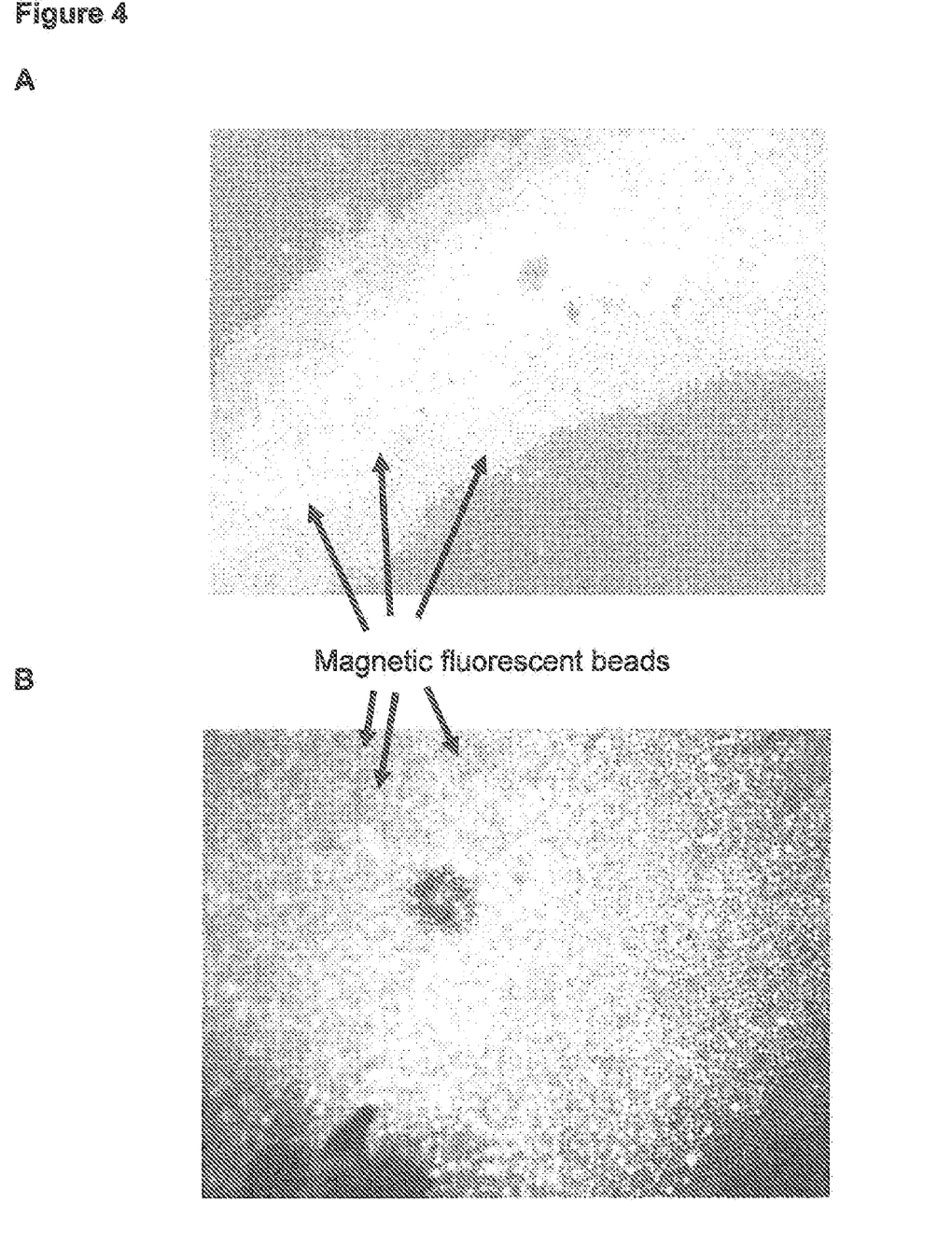
FIG. 4: (A) is an image of fluorescent beads on the face of the floater. The face has a thickness of 0.17 millimeters. (B) is an image of magnetic beads on the face of the floater. The face has a thickness of 0.7 millimeters.

FIG. 4A displays a fluorescence image of magnetic green fluorescent beads (Bangs beads), having a diameter of 8 microns. The beads are collected on the face of a floater using a 1/32"×1/16" neodymium permanent disc magnet with the face having a thickness of 0.17 millimeters. FIG. 4B shows the magnetic beads imaged on the face of the floated.

Figure 5:
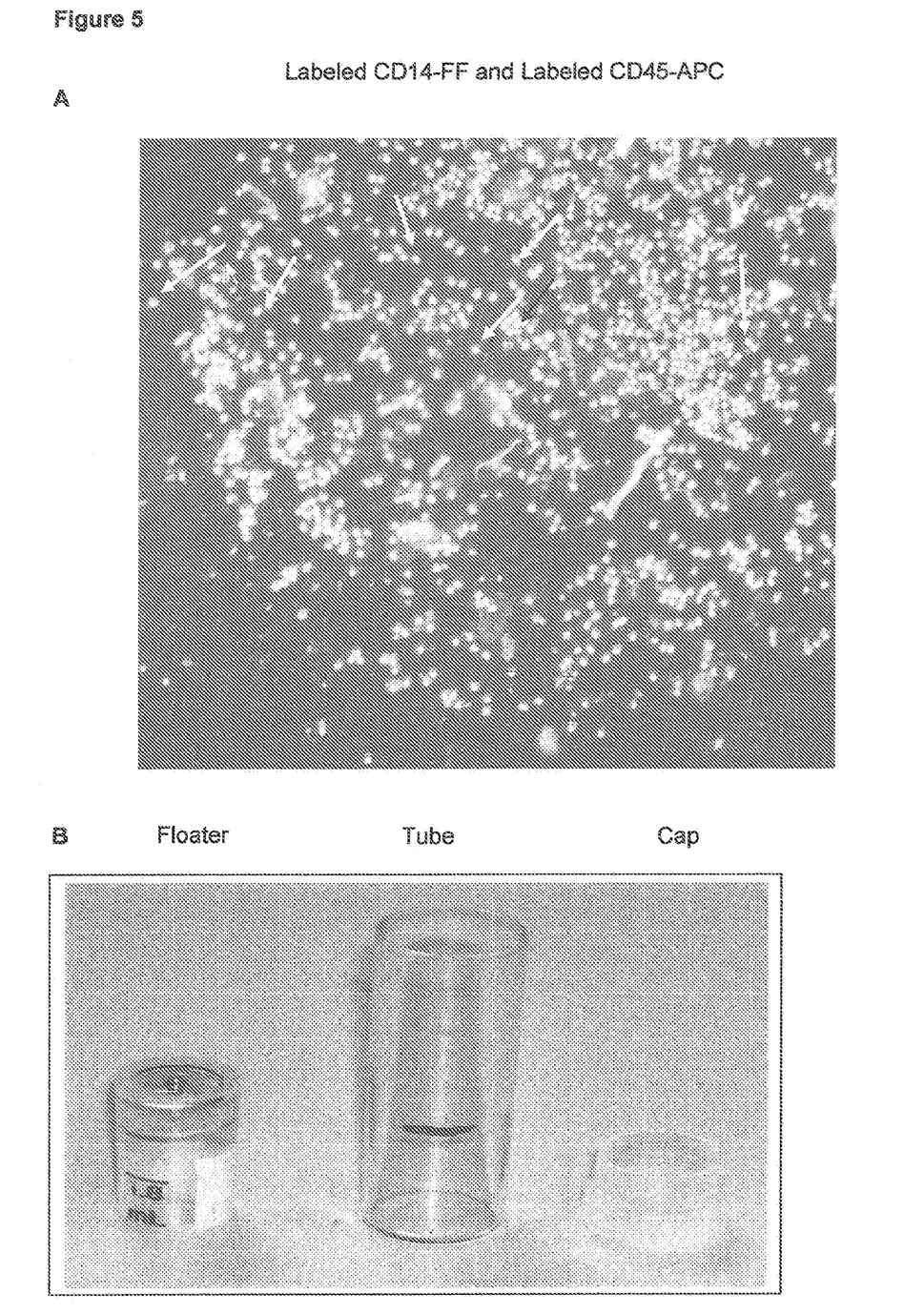
FIG. 5: (A) shows an image of CD14-FF selected cells after staining with Acridine Orange and CD45-APC. (B) From left to right, the floater, the tube with chamber having a line to mark the volume, and the cap of the chamber.

FIG. 5A displays an overlay image of CD14-FF selected cells that were collected on the face of a floater with an outside diameter of 12 mm using a 1/16"×1/4" neodymium cylinder magnet and a face thickness of 2 cover slips, approximately 0.34 mm. The intensity of Acridine Orange can be shown as a green signal to distinguish the red color for the CD45-APC label. FIG. 5B shows the floater, the chamber, and the cap of the chamber.

For each sample preparation, 200 μl of blood from a blood preservative tube CELLSAVE™ Preservative Tube, Immunicon Corporation) was incubated for 10 minutes with 10 μl CD14-FF (0.88 g/ml), 10 μl Acridine Orange (1 mM) and 10 μl CD45-APC in a glass chamber, as shown in FIG. 5A. Phosphate buffered saline (PBS; 2 ml) was added to fill the chamber to a predetermined amount. The floater is added to the chamber with the side containing the magnet facing the glass bottom of the chamber. The chamber was rotated to ensure complete mixing. After 10 minutes the chamber was inverted and the cells collected on the face of the magnet were fluorescently imaged.

Example 1

CD-CHEX®, a whole blood assay control, Capture Efficiency To determine the capture efficiency with known absolute numbers of leukocytes and their phenotypes is used.

Materials and Methods:
CD-CHEX®, a whole blood assay control, (lot # 60650071):
CD3+: 1859/μl
CD3+/CD4+: 1221/μl
CD3+/CD8+: 576/μl To 50 μl of CD-CHEX®, a whole blood assay control, add 10 μl of CD3-FF (clone Cris7), 10 μl of CD4-APC and 10 μl of CD8-PE. After 25 minutes of incubation, 10 μl of this solution is injected into the chamber. PBS (1.8 ml) is added with 100 μl DAPI. The floater is then inserted. After capping, the chamber is placed on a rocker and rotated overnight (approximately 16 hrs). The chamber is inverted and the images of the floater are acquired.

Figure 6:
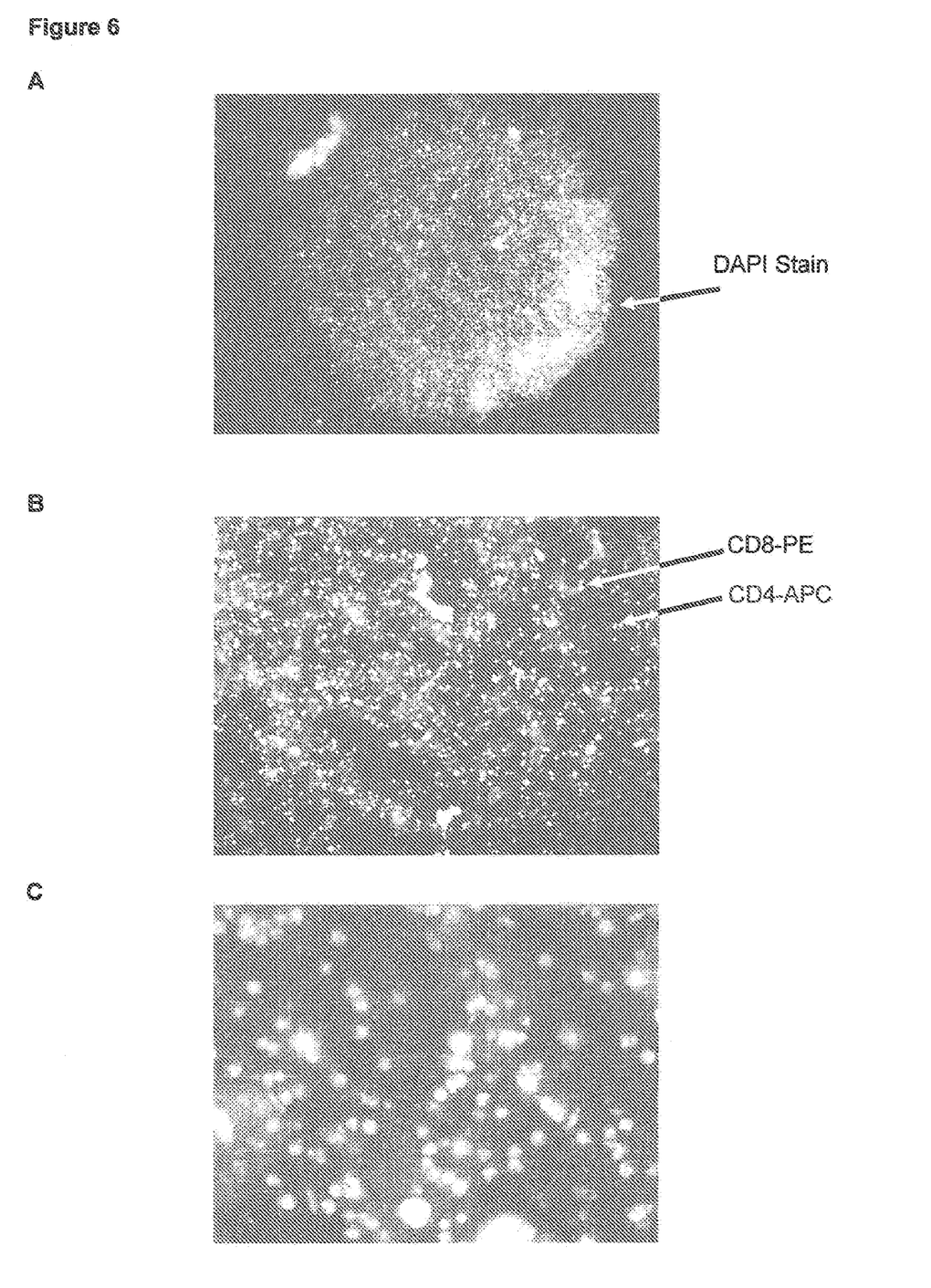
FIG. 6: Fluorescent images acquired using three different objectives. (A) Image acquired using 5×NA 0.12 objective (DAPI stain is indicated by the arrow). (B) images acquired using 10×, NA 0.25 (CD8-PE and CD4-APC are indicated by the arrow) and a (C) image using 40×, NA 0.6 objective.

Results:
For 100% capture efficiency, the floater surface contains:
CD3+: 10328 cells
CD3+/CD4+: 6783 cells
CD3+/CD8+: 3200 cells
Images are acquired with different objectives and the resulting over-lay images are presented as shown in FIG. 6.

FIG. 6A displays the image acquired using a 5×NA 0.12 objective. Figures B and C are acquired using a 10×, NA 0.25 and a 40×, NA 0.6 objective, respectively. The blue color represents the DAPI, green is CD8-PE and red is CD4-APC. With the number of CD8-PE (green) labeled cells expected to be 3200 and the actual number of CD8-PE labeled cells equal to approximately 500, the capture efficiency will be 16%.

Example 2

Comparison Between Two Methods for Using Permanent Magnetics

To determine the imaging of control cells after analysis using a CELLTRACKS® imaging device and a method of inserting and removing a magnetic from the cell suspension (method 1) and using the method with a permanent magnet fixed to a floater (method 2) as described in the present invention.

Materials and Methods:
After analysis using the CELLTRACKS® System, a system for image analysis of single cells, control cells from the cartridge were transferred to a chamber similar to FIG. 5B. The cartridge was washed several times with PBS using a pasteur pipette and all fluid used in the wash (approximately 500 microliters) was transferred to the chamber. Additional PBS was added to the volume to bring the total volume to 2 ml. Vial was placed on the tube rotator. The rotation speed was set so the floater moved through the entire fluid in one rotation. After complete mixing, 1.5 ml of control cells was injected into the vial together with 50 μl of Epcam ferrofluid and 10 μl of DAPI reagents (CellSearch™, Veridex LLC). After 30 minutes of incubation images were acquired at multiple points in time.

Figure 7:
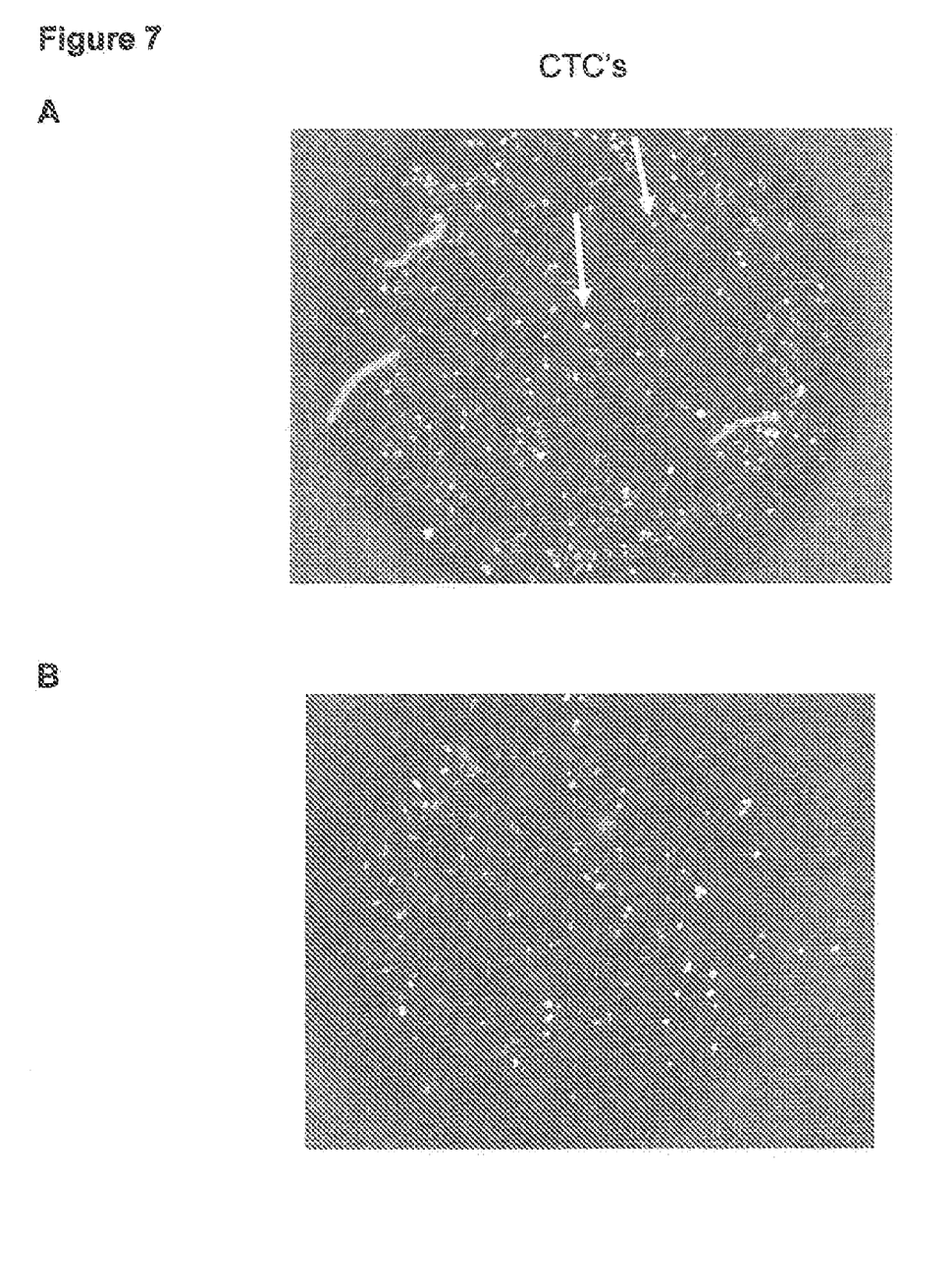
FIG. 7: Images obtained from two methods. (A) shows results obtained after 40 rotations using method 1. (B) shows the results from method 2, obtained after 500 rotations.

Results:

Method 1.
The image in FIG. 7A shows results after 40 rotations. Image quality is suitable for cells to be counted easily. The number of green cells corresponds to highs at 556 circulating tumor cells (CTC) and low at 47 CTC. After 100 rotations most of cells become buried under a layer of ferrofluids. At this point, cells are not visible and can not be counted.

Method 2.
The image in FIG. 7B was acquired after more than 500 rotations. In spite of the lower amount of ferrofluid the image quality is still sufficient to count the cells. Number of cells is the following: High: 209 Low: 25 with expected, high 435, low 23. Accordingly, the recovery is 45% for high and 100% for the low.

Example 3

Amount of Ferrofluid

To determine the quality of image with increasing ferrofluid. As the amount of ferrofluid increases the image quality decreases. Cells become buried under a layer of ferrofluid and are invisible for detection. This results, in part, in the low recoveries.

Materials and Methods:
COMPEL Magnetic Microspheres, Dragon green, 2.914 $10^7$/ml, diameter 8.44 microns, lot#6548 (Bangs Laboratories Inc. Catalog code UMC4F) were diluted 1:100. System buffer (1.5 ml) was added to the glass vial and 50 microliters containing 14570 beads were added together with 20, 40, 60 and 80 microliters of EpCam ferrofluid (20 mg/ml). Fluorescence images were acquired after 15 and 30 minutes of rotation. Test tube rotator was set at 10 rpm, resulting in 150 and 300 rotations.

Floater is Corning 1/16" diameter magnet.

Figure 8:
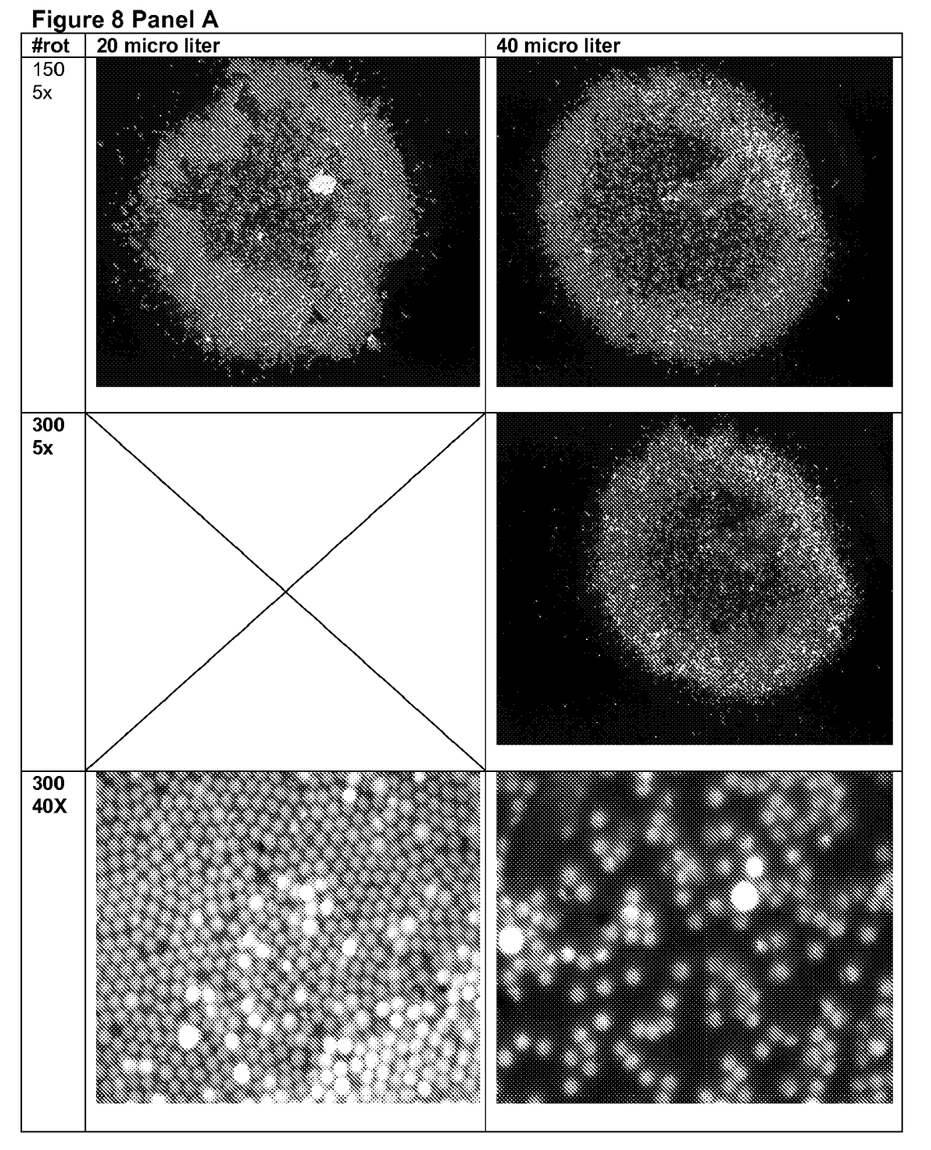
FIG. 8: Images obtained with a 5× and 40× objective with the addition of 20 and 40 microliters of EpCam ferrofluid (Panel A) and 60 and 80 microliters of EpCam ferrofluid (Panel B) (20 mg/ml).

Results:

Images are acquired with a 5×, 10× and 40× objectives. As shown in FIG. 8, 5× and 40× objectives were used to image 20 and 40 microliters of EpCam (Panel A) and 10× and 40× objectives were used to image 60 and 80 microliters of EpCam (Panel B). The missing images shown in FIG. 8 were lost during saving.

Example 4

Assessing Capture Efficiency

To determine the capture efficiency of different size magnets.

Materials and Methods:

Method A

1. After analysis of a CellTracks cartridge with control cells the contents of the cartridge was emptied. The contents of two cartridges were pooled. Exact number of controls cells that are removed from the cartridge is unknown since some are stuck to the glass. 100 ul of this cell suspension was transferred to the test tube and 1.5 ml of PBS was added.
2. Four test tubes were filled and in two a floater, Corning 1/16" diameter length 1/4" magnet was used and the other two a Corning 1/16" diameter length 1/2" was
3. Tubes were placed a tube rotator for 30 minutes. Rotation speed 10 RPM.
4. Floater was removed from test tube were placed in a Quadrupole magnet for 10 minutes. After 10 minutes the fluid was removed and replaced by 300 microliter of PBS. Tube was removed and vortexed.
5. The 300 micoliters were transferred to cartridge and cartridge was rescanned to see how many cells remained in the fluid.
6. Efficiency was calculated by dividing the number of cells on the floater by the number of cells found in the rescan of the remaining fluid.

Results:

| Magnet | Floater | CellTracks rescan | Cap efficiency |
|---|---|---|---|
| 1/16 × 1/4" | 256 | 1 | 99.6% |
| 1/16 × 1/4" | 225 | na | na |
| 1/16 × 1/2" | 230 | 2 | 99.1 |
| 1/16 × 1/2" | 218 | na | na |

Method B

1. After analysis of a cartridge used in the cell imaging and analysis system, CELLTRACKS™ with control cells the contents of the cartridge was emptied. Cartridges can be pooled if large number of cells is required. Exact number of controls cells that are removed from the cartridge is unknown since some are stuck to the glass. 100 μl of this cell suspension was transferred to the test tube and 1.5 ml of PBS was added.
2. Two types of floaters, Corning 1/16" diameter length 1/4" magnet and a Corning 1/16" diameter length 1/2".
3. Tubes were placed a tube rotator for 15 minutes. Rotation speed 10 RPM.
4. Floater was removed from the tubes and the tube with the remaining fluid was placed inside the Quadrupole magnet for 10 minutes. After 10 minutes the fluid was removed and replaced by 300 microliter of PBS. Tube was removed from the Quadrupole and vortexed.
5. 300 micoliter was transferred to a cartridge for the CELLTRACKS® imaging device and placed inside the magnetic presentation device MAGNEST™ and after 15 minutes rescanned on CELLTRACKS®.
6. Efficiency was calculated by dividing the number of cells on the floater by the number of cells found in the rescan of the remaining fluid.

Results:

| | Floater | | CellTracks rescan | | Cap efficiency | |
|---|---|---|---|---|---|---|
| Magnet | Low | High | Low | High | Low | High |
| 1/16 × 1/4" | 13 | 173 | 0 | 0 | 100 | 100 |
| 1/16 × 1/4" | 31 | 274 | 0 | 13 | 100 | 95 |
| 1/16 × 1/2" | 11 | 136 | 0 | 2 | 100 | 98 |
| 1/16 × 1/2" | 13 | 318 | 0 | 15 | 100 | 95 |

Method C

1. After analysis of a cartridge with control cells the contents of the cartridge was emptied. Cartridges can be pooled if large number of cells is required. Exact number of controls cells that are removed from the cartridge is unknown since some are stuck to the glass.
2. Cell suspension two fold diluted with Instrument buffer and 100 μl of this cell suspension was transferred to the test tube and 1.5 ml of PBS was added.
3. Two types of floaters, Corning 1/16" diameter length 1/4" magnet and a Corning 1/16" diameter length 1/2".
4. Tubes were placed a tube rotator. Rotation speed 10 RPM.
5. Number of cells collected was determined at 1, 2, 3, 4, 5, 7, 10, and 15 minutes.
6. Cells were identified on DAPI and DIOC.

Figure 9:
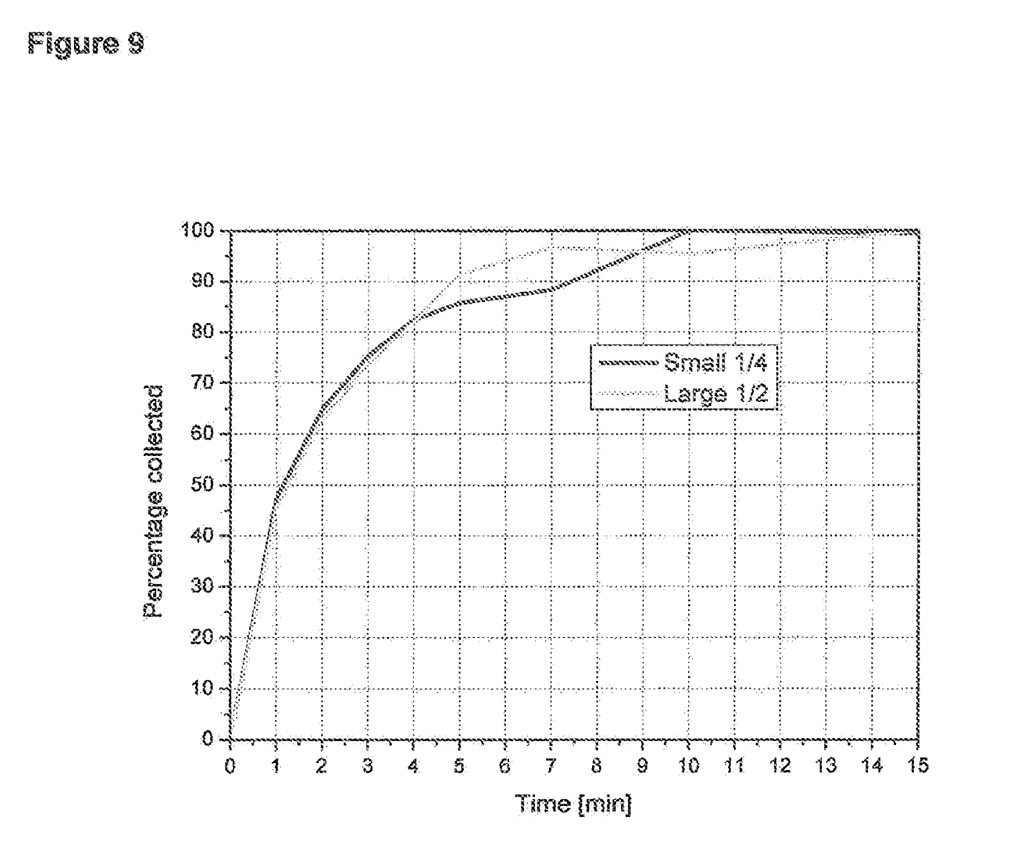
FIG. 9: Graph representing the number of cells collected as a function of time with small ($\frac{1}{16}\times\frac{1}{4}$") and large magnets ($\frac{1}{16}\times\frac{1}{2}$").

Results:

The graph in FIG. 9 shows the number of cells collected as a function of time While certain of the preferred embodiments of the present invention have been described and specifically exemplified above, it is not intended that the invention be limited to such embodiments. Various modifications may be made thereto without departing from the spirit of the present invention, the full scope of the improvements are delineated in the following claims.

What is claimed is:

1. A method for detecting and enumerating a target population within a biological specimen, comprising:
    a. adding a sample of said biological specimen to a chamber;
    b. labeling said target population within said biological specimen in the sample with a fluorescent marker wherein said marker is specific for said target population;
    c. coupling said target population to a magnetic particle;

d. adding a floater containing a small permanent magnet directly to said specimen whereby said target population is oriented along one face of said floater;
e. allowing the floater to stabilize along the viewing window of the chamber;
f. acquiring an image of said target population, and
g. analyzing said image to detect and enumerate said labeled target population.

2. The method of claim 1 wherein said target population is CD4 expressing cells.

3. The method of claim 1 wherein said magnet is neodymium.

4. The method of claim 1 wherein said magnet is a disc having a diameter of about 1.6 mm and a height of 0.8 mm.

5. The method of claim 1 wherein said magnet is coated with polydimethylsiloxane (PDMS) silicone.

* * * * *